United States Patent
Kujundzic et al.

(10) Patent No.: US 7,365,056 B2
(45) Date of Patent: Apr. 29, 2008

(54) SUBSTITUTED 9A-N-(N'-(SULFONYL)PHENYLCARBAMOYL)DERIVATIVES OF 9-DEOXO-9-DIHYDRO-9A-AZA-9A-HOMOERITHOMYCIN A AND 5-0-DESOSAMINYL-9-DEOXO-9-DIHYDRO-9-A-AZA-9A-HOMOERITHRONOLIDE A

(75) Inventors: Nedjeljko Kujundzic, Zagreb (HR); Mirjana Bukvic Krajacic, Zagreb (HR); Karmen Brajsa, Zagreb (HR)

(73) Assignee: GlaxoSmithKline istrazivacki centar Zagreb d.o, Zagreb (HR)

( * ) Notice: Subject to any disclaimer, the term of this patent is extended or adjusted under 35 U.S.C. 154(b) by 25 days.

(21) Appl. No.: 10/534,628

(22) PCT Filed: Nov. 10, 2003

(86) PCT No.: PCT/HR03/00058

§ 371 (c)(1),
(2), (4) Date: Oct. 5, 2005

(87) PCT Pub. No.: WO2004/043985

PCT Pub. Date: May 27, 2004

(65) Prior Publication Data

US 2006/0084795 A1    Apr. 20, 2006

(30) Foreign Application Priority Data

Nov. 11, 2002  (HR) .................. P 20020885 A

(51) Int. Cl.
    A61K 31/70   (2006.01)
    C07H 17/08   (2006.01)
(52) U.S. Cl. .................... 514/29; 536/7.3; 536/7.4
(58) Field of Classification Search .......... 536/7.3, 536/7.4; 514/29
    See application file for complete search history.

(56) References Cited

U.S. PATENT DOCUMENTS

| | | | |
|---|---|---|---|
| 4,328,334 A | 5/1982 | Kobrehel et al. | |
| 4,474,768 A | 10/1984 | Bright et al. | |
| 4,492,688 A | 1/1985 | Bright | |
| 5,629,296 A | 5/1997 | Kujundzic et al. | |
| 6,852,702 B2 | 2/2005 | Kujundzic et al. | |
| 6,872,707 B1 | 3/2005 | Marusic-Istuk et al. | |

FOREIGN PATENT DOCUMENTS

| | | |
|---|---|---|
| BE | 892397 | 1/1982 |
| EP | 0316 128 | 7/1981 |
| EP | 0132 944 | 12/1986 |
| EP | 0657 464 | 10/1996 |
| FR | 2473525 | 3/1993 |
| WO | WO 97/35590 | 10/1997 |
| WO | 0066603 | 11/2000 |
| WO | WO/2002/12260 | 2/2002 |
| WO | WO/2002/068438 | 9/2002 |
| WO | WO 2004/043894 | 5/2004 |
| WO | WO 2004/052904 | 6/2004 |

OTHER PUBLICATIONS

McGuire [Antibiotics and Chemotherapy, vol. 11, No. 6 (Jun. 1952) 281-283].
P. Kurath et al., Experientia 27/4 (1971) 362.
S. E Djokic et al., Tetrahedron Letters, No. 17, Apr. 1967: 1645-1647.
R. S. Egan et al., J. Org. Chem. No. 17, vol. 39 (Aug. 1974) 2492-2494.
P. Lugar et al., Journal of Crystal and Molecular Structure, vol. 9, No. 6 (Dec. 1979) 329-338.
Journal of Antibiotics, vol. 46, No. 8 (Jan. 1993) 1239-1245 (G. Kobrehel et al.).
Azalides: synthesis and antibacterial activity of novel 9a-N-(N'substituted carbamoyl and thiocarbamoyl) derivatives of 9-deoxo-9a-aza-9a-homoerythromycin A; N Kujundzic et al., PLIVA, Research Institute, Eur J. Med Chem (1995) 30, 455-462.

*Primary Examiner*—Elli Peselev
(74) *Attorney, Agent, or Firm*—Karen L. Prus

(57) ABSTRACT

The invention relates to substituted 9a-N-{N'-[4-(sulfonyl)phenyl]carbamoyl} derivatives of 9-deoxo-9-dihydro-9a-aza-9a-homoerythromycin A and 5-0-desosaminyl-9-deoxo-9-di-hydro-9a-aza-9a-homoerithronolide A, novel semisynthetic macrolide antibiotics of the azalide series general formula (1), wherein R represents H or cladinosyl moiety and R1 represents chloro, amino, phenylamino, 2-pyridylamino, 3,4-dimethyl-4-isoxalylamino and 5-methyl-3-isoxazolylamino group, and pharmaceutically acceptable addition salts thereof with inorganic or organic acids. to the process for their preparation of pharmaceutical composition as well as the use their compositions for sterilization rooms and medical instruments as well as for protection of wall and wooden coatings

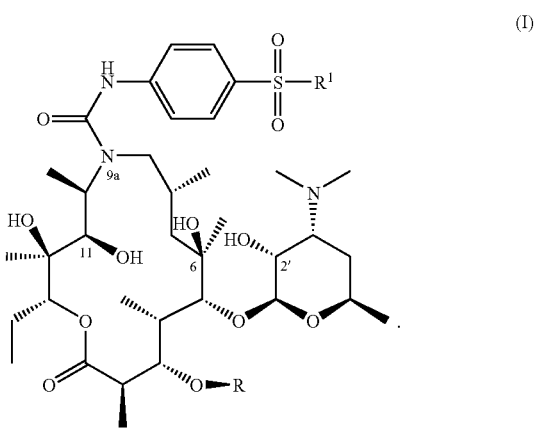

(I)

20 Claims, No Drawings

SUBSTITUTED 9A-N-(N'-(SULFONYL)PHENYLCARBAMOYL)DERIVATIVES OF 9-DEOXO-9-DIHYDRO-9A-AZA-9A-HOMOERITHOMYCIN A AND 5-0-DESOSAMINYL-9-DEOXO-9-DIHYDRO-9-A-AZA-9A-HOMOERITHRONOLIDE A

TECHNICAL FIELD

Int. Cl. C07H17/08, A61K31/71

TECHNICAL PROBLEM

The present invention relates to substituted 9a-N-{N'-[4-(sulfonyl)phenylcarbamoyl]} derivatives of 9-deoxo-9-dihydro-9a-aza-9a-homoerithromycin A and 5-O-desosaminyl-9-deoxo-9-dihydro-9a-aza-9a-homoerithronolide A, novel semisynthetic macrolide antibiotics of the azalide series having antibacterial activity of the general formula 1

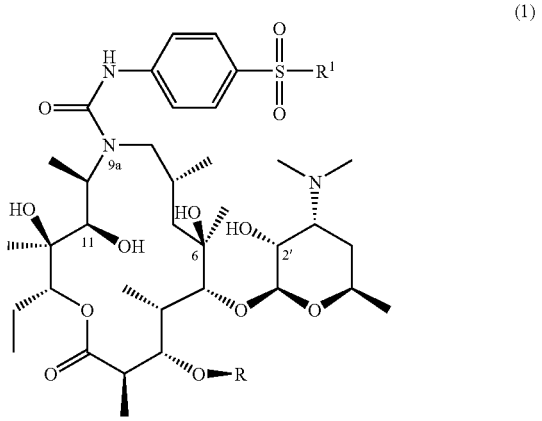

(1)

wherein R represents H or cladinosyl moiety, and $R^1$ represents chloro, amino, phenylamino, 2-pyridylamino, 3,4-dimethyl-5-isoxazolylamino and 5-methyl-3-isoxasolylamino group, to pharmaceutically acceptable addition salts there of with inorganic or organic acids, to a process for the preparation of the pharmaceutical compositions as well as to the use of pharmaceutical compositions obtained in the treatment of bacterial infections.

PRIOR ART

Erythromycin A is a macrolide antibiotic, whose structure is characterized by 14-membered macrolactone ring having carbonyl group in C-9 position. It was found by McGuire in 1952 [Anitibiot. Chemotiher., 2 (1952) 281] and for over 50 years it has been considered as a reliable and effective antimicrobial agent in the treatment of diseases caused by Gram-positive and some Gram-negative microorganisms. However, in an acidic medium it is easily converted into anhydroerythromycin A, an inactiv C-6/C-12 metabolite of a spiroketal structure [P. Kurath et al., Experientia 27 (1971) 362]. It is well-known that spirocyclisation of aglycone ring of erythromycin A is successfully inhibited by a chemical transformation of C-9 ketones or hydroxy groups in C-6 and/or C-12 position. By the oximation of C-9 ketones [S. Dokić et al., Tetrahedron Lett. 1967: 1945] and by subsequently modifying the obtained 9(E)-oxime into 9-[O-(2-methoxyethoxy)methyloxime] erythromycin A (ROXITHROMYCIN) [G. S. Ambrieres, Fr. Pat. 2,473,525, 1981] or 9(S)-erithromycylamine [R. S. Egan et al., J. Org. Chem. 39 (1974) 2492] or a more complex oxazine derivative thereof, 9-deoxo-11-deoxy-9,11-{imino[2-(2-methoxyethoxyethylidene]-oxy}-9(S)-erythromycin A (DIRITHROMYCIN) [P. Lugar i sur., J. Crist. Mol. Struct. 9 (1979) 329], novel semisynthetic macrolides were synthetised, whose basic characteristic, in addition to a greater stability in an acidic medium, is a better pharmacokinetics and a long half-time with regard to the parent antibiotic erythromycin A. In a third way for modifying C-9 ketones use is made of Beckmann rearrangement of 9(E)-oxime and of a reduction of the obtained imino ether (G. Kobrehel i sur., U.S. Pat. No. 4,328,334, 1982.) into 11-aza-10-deoxo-10-dihydroerythromycin A (9-deoxo-9a-aza-9a-homoerythromycin A) under broadening the 14-member ketolactone ring into a 15-member azalactone ring. By reductive N-methylation of 9a-amino group according to Eschweiler-Clark process (G. Kobrehel et al., BE Pat. 892,397, 1982.) or by a preliminary protection of amino group by means of conversion into the corresponding N-oxides and then by alkylation and reduction [G. M. Bright et al., U.S. Pat. No. 4,474,768, 1984.] N-methyl-11-aza-10-deoxo-10-dihydroerythromycin A (9-deoxo-9a-methyl-9a-aza-9a-homoerithromycin A, AZITHROMYCIN) was synthetized, a prototype of azalide antibiotics, which, in addition to a broad antimicrobial spectrum including Gram-negative bacteria and intrcellular microorganisms, are characterized by a specific mechanism of transport to the application site, a long biological half-time and a short therapy period. In EP A 0316128 (G. M. Bright et al.) novel 9a-allyl and 9a-propargyl derivatives of 9-deoxo-9a-aza-9a-homoerythromycin A are disclosed and in U.S. Pat. No. 4,492,688, January 1985 (Bright G. M.) the synthesis and the antibactertial activity of the corresponding cyclic ethers are disclosed. In the J. Antibiotics 46 (1993) 1239 (G. Kobrehel et al.) there are further disclosed the syntesis and the activity spectrum of novel 9-deoxo-9a-aza-11-deoxy-9a-homoerythromycin A 9a,11-cyclic carbamates and O-methyl derivatives thereof.

According to the known and established Prior Art, 9a-N-{N'-[4-(sulfonyl)phenylcarbamoyl]} derivatives of 9-deoxo-9-dihydro-9a-aza-9a-homoerithromycin A and 5-O-desosaminyl-9-deoxo-9-dihydro-9a-aza-9a-homoerithronolide A and pharmaceutically acceptable addition salts thereof with inorganic or organic acids, a process for the preparation thereof as well as the preparation methods and use a pharmaceutical preparations have not been disclosed as yet.

It has been found and it is object of the present invention that substituted 9a-N-{N'-[4-(sulfonyl)phenylcarbamoyl]} derivatives of 9-deoxo-9-dihydro-9a-aza-9a-homoerithromycin A and 5-O-desosaminyl-9-deoxo-9-dihydro-9a-aza-9a-homoerithronolide A, novel semisynthetic macrolide antibiotics of the azalide series and pharmaceutically acceptable addition salts thereof with inorganic or organic acids may be prepared by reacting ammonia or substituted amine with 9a-N-[N'-[4-sulfonylphenyl)carbamoyl] derivatives of 9-deoxo-9-dihydro-9a-aza-9a-homoerithromycin A and 5-O-desosaminyl-9-deoxo-9-dihydro-9a-aza-9a-homoerithronolide A which are obtained by reacting of -9-deoxo-9-dihydro-9a-aza-9a-homoerithromycin A and 5-O-desosaminyl-9-deoxo-9-dihydro-9a-aza-9a-homoerithronolide A with 4-(chlorosulfonyl)phenylisocyanate and optionally by reacting the obtained 9a-N-{N'-[4-(sulfonyl)phenyl]carbamoyl} derivatives of 9-deoxo-9-dihydro-9a-aza-9a-homoerithromycin A and 5-O-desosaminyl-9-deoxo-9-dihydro-9a-aza-9a-homoerithronolide A with inorganic and organic acids.

TECHNICAL SOLUTION

It has been found that novel substituted 9a-N-{N'-[4-(sulfonyl)phenylcarbarnoyl]} derivatives of 9-deoxo-9-dihydro-9a-aza-9a-homoerithromycin A and 5-O-desosaminyl-9-deoxo-9-dihydro-9a-aza-9a-homoerithronolide A of the general formula 1, wherein R represents H or cladinosyl group and $R^1$ represents chloro group,

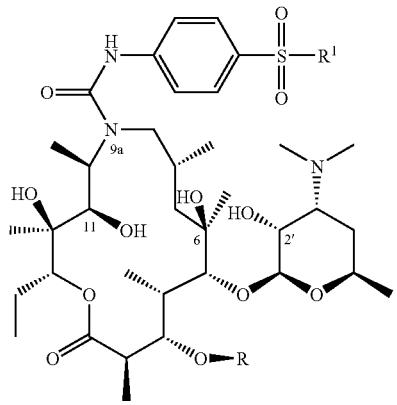
(1)

may be prepared by reacting 9-deoxo-9-dihydro-9a-aza-9a-homoerithromycin A and 5-O-desosaminyl-9-deoxo-9-dihydro-9a-aza-9a-homoerithronolide A of the general formula 2,

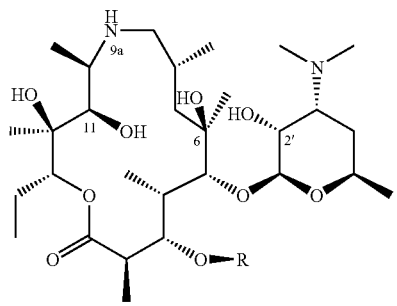
(2)

wherein R represents H or cladinosyl group, with 4-(chlorosulfonyl)phenylisocyanate formula 3,

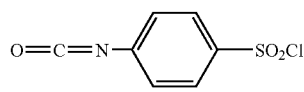
3 after that the compounds of general formula 1 were obtained, in which R has previous meaning, and $R^1$ represents Cl, by reaction of the compounds general formula 1 respectively, wherein R represents H or cladinosyl group and $R^1$ represents Cl, with ammonia or substituted amins general formula 4, wherein $R^2$ represents H, phenyl group, 2-pyridyl group, 3,4-dimethyl-5-isoxazolyl group or 5-methyl-3-isoxazolyl group,

$R^2—NH_2$      4 in toluene, xylene or some other aprotic solvent, at a temperature of 0° C. to 110° C. Pharmaceutically acceptable acid addition salts which also represents an object of the present invention, were obtained by reaction of substituted 9a-N-{N'-[4-(sulfonyl)phenylcarbamoyl]} derivatives of 9-deoxo-9-dihydro-9a-aza-9a-homoerithromycin A and 5-O-desosaminyl-9-deoxo-9-dihydro-9a-aza-9a-homoerithronolide A with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzene sulfonic acid, metane sulfonic acid, lauryl sulfonic acid, stearic acid, palmitic acid, succinic acid, ethylsuccinic acid, lactobionic acid, oxalic acid, salicylic acid and similiar acids, in a solvent inert to the reaction. Addition salts are isolated by evaporating the solvent or, alternatively, by filtration after a spontaneous precipitation or a precipitation by the addition of a non-polar cosolvent.

Substituted 9a-N-{N'-[4-(sulfonyl)phenylcarbamoyl]} derivatives of 9-deoxo-9-dihydro-9a-aza-9a-homoerithromycin A and 5-O-desosaminyl-9-deoxo-9-dihydro-9a-aza-9a-homoerithro-nolide A of the general formula 1 and pharmaceutically acceptable addition salts with inotganic or organic acids thereof possess an antibacterial activity in vitro.

Minimal inhibitory concentration (MIC) is defined as the concentration which shows 90% growth inhibition, and was determinated by broth dilution methods according to National Committe for Clinical Laboratory Standards (NC-CLS, M7-A2) protocols. Final concentration of test substances were in range from 64 to 0.125 µg/ml. MIC levels for all compound were determinated on panel of susceptible and resistant Gram positive bacterial strains (*S. aureus, S. pneumoniae* and *S. pyogenes*) and on Gram negative strains (*E. coli, H. influenzae, E. faecalis, M. catarrhalis*).

Test substances from Example 3 to 7 were active on susceptible strains of *S. pyogenes* (MIC 2 to 8 µg/ml), and on susceptible strains on *S. pneumoniae* (MIC 0.5 to 8 µg/ml). Substances from Example 3 and 4 showed showed strong antimicrobial activities on *S. pyogenes* iMLS resistante strain (MIC 2 µg/ml).

The obtained results for substances from Example 3 to 7 expressed as MIC in mg/ml suggest a potentional use thereof as sterilization agents of e.g. rooms and medical instruments and as industrial microbial agents e.g. for the protection of wall and wooden coatings.

Process for the preparation of 9a-N-{N'-[4-(sulfonyl)phenyl)carbamoyl} derivatives of 9-deoxo-9-dihydro-9a-aza-9a-homoerithromycin A and 5-O-desozaminyl-9-deoxo-9-dihydro-9a-aza-9a-homoerithronolide A of this invention is illustrated by the following Examples which should in no way be construed as a limitation of the scope thereof.

EXAMPLE 1

9-Deoxo-9-dihydro-9a-N-{[4-(chlorosulfonyl)phenyl]carbamoyl}-9a-aza-9a-homoerithromycin A A mixture of 1.35 g (1.84 mmol) 9-deoxo-9-dihydro-9a-aza-9a-homoerithromycin A and 0.40 (1.84 mmol) 4-(chlorosulfonyl)phenylisocyanate and 30 ml dry toluene was stirred 1 hour at the temperature 0-5° C. The reaction mixture was evaporated at reduced pressure to dryness to give crude 9-deoxo-9-dihydro-9a-N-{[4-(chlorosulfonyl)phenyl]carbamoyl}-9a-aza-9a-homoerithromycin A. The pure product was obtained, where from by chromatography the crude product on a sillica gel column using solvent methylene chloride.

MS(ES$^+$) m/z=794.

EXAMPLE 2

5-O-Desosaminyl-9-deoxo-9-dihydro-9a-N-{[4-(chlorosulfonyl)phenyl]carbamoyl}-9a-aza-9a-homoerithronolide A Analogously to the process disclosed in Example 1, from 1.95 g (2.0 mmol) 5-O-desosaminyl-9-deoxo-9-dihydro-9a-aza-9a-homoerithronolide A and 0.43 g (2.0 mmol) 4-(chlorosulfonyl)phenylisocyanate in 30 ml dry toluene crude product was obtained, wherefrom by chromatography on sillica gel column using methylene chloride as a solvent. Pure 5-O-desosaminyl-9-deoxo-9-dihydro-9a-N-{[4-(chlorosulfonyl)phenyl]-carbamoyl}-9a-aza-9a-homoerithronolide A was obtained.

MS (ES+) m/z=794.

EXAMPLE 3

9-Deoxo-9-dihydro-9a-N-{[4-(aminosulfonyl)phenyl]carbamoyl}-9a-aza-9a-homoerithromycin A The solution of 1.35 g (1.84 mmol) 9-deoxo-9-dihydro-9a-aza-9a-homoerithromycin A and 0.4 g (1.84 mmol) 4-(chlorosulfonyl)phenyl isocyanate in 30 ml dry toluene was stirred about 1.0 hour at the temperature 0°-5° C. In the reaction mixture 5.0 ml (4.55 g; 61.5 mmol) 23% water solution of ammonia was added and the reaction mixture was stirred about 30 minutes at room temperature. The crude product was filtered, wherefrom by column chromatography on silica gel using solvent system methylen-chloride:methanol=9:1. Pure 9-deoxo-9-dihydro-9a-N-{[4-(aminosulfonyl)phenyl]-carbamoyl}-9a-aza-9a-homoerithromycin A was obtained.

IR (KBr)/cm$^{-1}$=1727, 1638, 1593, 1552, 1126, 1013. $^1$H NMR (500 MHz; CDCl$_3$/δ)=4.41 (1H, H-1'), 4.76 (1H, H-1"), 4.00 (1H, H-3), 3.41 (1H, H-5), 3.20 (3H, 3"-OCH$_3$), 2.89 (1H, 4"), 2.50 (6H, 3'-N'(CH$_3$)$_2$), 2.26 (1H, H-2"a), 1.51 (1H, H-2"b), 1.29 (1H, H-8), 0.96 (3H, 10-CH$_3$), 0.89 (3H 4-CH$_3$), 0.80 (3H, H-15).

$^{13}$C NMR (500 MHz; CDCl$_3$/δ)=175.6 (C-1), 155.5 (9a-N CONH), 101.9 (C-1'), 95.2 (C-1"), 84.1 (C-5), 78.3 (C-3), 48.8 (3"-OCH$_3$), 44.5 (C-2), 27.6 (C-8), 19.9 (8-CH$_3$), 9.2 (10-CH$_3$), 11.1 (C-15).

MS (ES$^+$) m/z (%)=933.

EXAMPLE 4

9-Deoxo-9-dihydro-9a-N-{N'-[4-(phenylaminosulfonyl)phenyl]carbamoyl}-9a-aza-9a-homoerithromycin A Analogously to the process disclosed in Example 3, from 1.35 g (1.84 mmol) 9-deoxo-9-dihydro-9a-aza-9a-homoerithromycin A, and 0.4 g (1.84 mmol) 4-(chlorosulfonyl)phenyl isocyanate, 1.0 ml (11.0 mmol) aniline in 30 ml dry toluene 0.8 g pure 9-deoxo-9-dihydro-9a-N-{N'-[4-(aminosulfonyl)phenyl]carbamoyl-}a-aza-9a-homoerithromycin A was obtained with following spectral data.

IR (KBr)/cm$^{-1}$=1727, 1638, 1593, 1552, 1126, 1013.

$^1$H NMR (500 MHz; CDCl3/δ)=4.45 (1H, H-1'), 4.76 (1H, H-1"), 4.01 (1H, H-3), 3.38 (1H, H-5), 3.2(3H, 3"-OCH$_3$), 2.90 (1H, 4"), 2.50 (6H, 3'-N'(CH$_3$)$_2$), 2.26 (1H, H-2"a), 1.52 (1H, H-2"b), 1.27 (1H, H-8), 0.90 (3H, 10-CH$_3$), 0.89 (3H 4-CH$_3$), 0.79 (3H, H-15).

$^{13}$C NMR (500 MHz; CDCl3/δ)=179.0 (C-1), 155 (9a-N CONH), 103.8 (C-1'), 95.8 (C-1"), 84.7(C-5), 79.0 (C-3), 50.0 (3"-OCH$_3$), 46.5 (C-2), 27.9 (C-8), 20.4 (8-CH$_3$), 9.2 (10-CH$_3$), 11.3 (C-15).

MS (ES$^+$) m/z (%)=1009.

EXAMPLE 5

9-Deoxo-9-dihydro-9a-N-{N'-[4-(2-pyridylaminosulfonyl)phenyl]carbamoyl}-9a-aza-9a-homoerithromycin A Analogously to the process disclosed in Example 3, from 1.35 g (1.84 mmol) 9-deoxo-9-dihydro-9a-aza-9a-homoerithromycin A, 0.4 g (1.84 mmol) 4-(chlorosulfonyl)phenyl isocyanate and 0.70 g (5.2 mmol) 2-aminopyridine in 30 ml dry toluene 0.5 g pure 9-deoxo-9-dihydro-9a-N-{N'-[4-(2-pyridylaminosulfonyl)phenyl]carbamoyl}-9a-aza-9a-homoerithromycin A was obtained with following spectral data.

IR (KBr)/cm$^{-1}$=1727, 1638, 1593, 1552, 1126, 1013.

$^1$H NMR (500 MHz; CDCl$_3$/δ)=4.41 (1H, H-1'), 4.75 (1H, H-1"), 4.00 (1H, H-3), 3.38 (1H, H-5), 3.21 (3H, 3"-OCH$_3$), 2.89 (1H, 4"), 2.50 (6H, 3'-N'(CH$_3$)$_2$), 2.27 (1H, H-2"a), 1.48 (1H, H-2"b), 1.27 (1H, H-8), 0.89 (3H, 10-CH$_3$), 0.88 (3H 4-CH$_3$), 0.79 (3H, H-15).

$^{13}$C NMR (500 MHz; CDCl$_3$/δ)=175.6 (C-1), 155.4 (9a-N CONH), 101.9 (C-1'), 95.1 (C-1"), 84.0 (C-5), 78.1 (C-3), 48.8 (3"-OCH$_3$), 46.5 (C-2), 27.6 (C-8), 19.9 (8-CH$_3$), 9.1 (10-CH$_3$), 11.1 (C-15).

MS (ES$^+$) m/z (%)=1014.

EXAMPLE 6

9-Deoxo-9-dihydro-9a-N-{N'-[4-(3,4-dimethyl-5-isoxazolylaminosulfonyl)phenyl]-carbamoyl}-9a-aza-9a-homoerithromycin A Analogously to the process disclosed in Example 3, from 1.35 g (1.84 mmol) 9-deoxo-9-dihydro-9a-aza-9a-homoerithromycin A, 0.4 g (1.84 mmol) 4-(chlorosulfonyl)phenyl isocyanate and 0.41 g (3.67 mmol) 5-amino-3,4-dimethyl-isoxazole in 30 ml dry toluene 1.5 g pure 9-deoxo-9-dihydro-9a-N-{N'-[4-(3,4-dimethyl-5-isoxazolylaminosulfonyl)-phenyl]carbamoyl}-9a-aza-9a-homoerithromycin A was obtained.

MS (ES$^+$) m/z (%)=1028.

EXAMPLE 7

9-Deoxo-9-dihydro-9a-N-{N'-[4-(5-methyl-3-isoxazolylaminosulfonyl)phenyl]-carbamoyl}-9a-aza-9a-homoerithromycin A Analogously to the process disclosed in Example 3, from 1.35 g (1.84 mmol) 9-deoxo-9-dihydro-9a-aza-9a-homoerithromycin A, 0.4 g (1.84 mmol) 4-(chlorosulfonyl)phenyl isocyanate and 0.36 g (3.67 mmol) 3-amino-5-methylisoxazole in 30 ml dry toluene 0.40 g pure 9-deoxo-9-dihydro-9a-N-{N'-[4-(5-methyl-3-isoxazolylaminosulfonyl)-phenyl]carbamoyl}-9a-aza-9a-homoerithromycin A was obtained with following spectral data.

$^1$H NMR (500 MHz; CDCl$_3$/δ)=4.42 (1H, H-1'), 4.75 (1H, H-1"), 4.01 (1H, H-3), 3.39 (1H, H-5), 3.20 (3H, 3"-OCH$_3$), 2.89 (1H, 4"), 2.50 (6H, 3'-N'(CH$_3$)$_2$), 2.24 (1H, H-2"a), 1.48 (1H, H-2"b), 1.28 (1H, H-8), 0.90 (3H, 10-CH$_3$), 0.87 (3H 4-CH$_3$), 0.79 (3H, H-15).

$^{13}$C NMR (500 MHz; CDCl$_3$/δ)=175.8 (C-1), 155.6 (9a-N CONH), 101.7 (C-1'), 95.8 (C-1"), 84.0 (C-5), 78.3 (C-3), 48.9 (3"-OCH$_3$), 45 (C-2), 27.8 (C-8), 20.2 (8-CH$_3$), 9 (10-CH$_3$), 11.3 (C-15).

MS (ES$^+$) m/z (%)=1014.

EXAMPLE 8

5-O-Desosaminyl-9-deoxo-9-dihydro-9a-N-[4-(aminosulfonylphenyl)carbamoyl]-9a-aza-9a-homoerithronolide A Analogously to the process disclosed in Example 3, from 1.15 g (2.0 mmol) 5-O-desosaminyl-9-deoxo-9-dihydro-9a-aza-9a-homoerithronolide A, 0.43 g (2.0 mmol) 4-(chlorosulfonyl)phenyl isocyanate and 5.0 ml (4.55 g; 61.5 mmol) 23% water solution of ammonia in 30 ml xylene 0.60 g pure 5-O-desosaminyl-9-deoxo-9-dihydro-9a-N-[4-(aminosulfonylphenyl)carbamoyl]-9a-aza-9a-homoerithronolide A was obtained with following spectral data.

$^1$H NMR (500 MHz; piridin/δ)=8.16, 7.93, 7.93, 7.5 (1H, fenilni), 5.60 (1H, H-13) 5.1 (1H, H-1'), 4.41 (1H, H-5) 4.30 (1H, H-3), 3.61 (1H, H-5'), 3.49 (1H, H-2'), 3.02 (1H, H-2), 2.61 (1H, H-3'), 2.21 (6H, 3'-N(CH$_3$)$_2$), 2.36 (1H, H-14a), 1.70 (1H, H-4'a), 1.87 (1H, H-14b), 1.69 (1H, H-4) 1.52 (1H, H-4'b), 1.58 (3H, 2-CH$_3$), 1.01 (3H, H-15).

$^{13}$C NMR (500 MHz; piridin/δ)=178 (C-1), 156.7 (NH CONH), 144.8, (fenil.), 133.2 (fenil.), 131.5, 129.3, 127.6, 115.3, (CH, fenil.), 103.3 (C-1'), 75.0 (C-13) 75.4 (C-3), 69.9 (C-5'), 69.2 (C-2') 68.0 (C-5), 65.4 (C-3') 45.6 (C-2), 40.3 (3'-N(CH$_3$)$_2$), 39.1 (C-4), 23.2 (C-14), 29.2 (C-4'), 16.7 (2-CH$_3$), 11.4 (C-15).

MS (ES$^+$) m/z (%)=775.

EXAMPLE 9

5-O-Desosaminyl-9-deoxo-9-dihydro-9a-N-{N'-[4-(phenylaminosulfonyl)phenyl]-carbamoyl}-9a-aza-9a-homoerithronolide A Analogously to the process disclosed in Example 3, from 1.15 g (2.0 mmol) 5-O-desosaminyl-9-deoxo-9-dihydro-9a-aza-9a-homoerithronolide A, 0.43 g (2.0 mmol) 4-(chlorosulfonyl)phenyl isocyanate and 0.4 ml (0.419 g, 4.4 mmol) aniline in 30 ml dry toluene 0.70 g pure 5-O-desosaminyl-9-deoxo-9-dihydro-9a-N-{N'-[4-(phenylamino-sulfonyl)phenyl]carbamoyl}-9a-aza-9a-homoerithronolide A was obtained with following spectral data.

$^1$H NMR (500 MHz; CDCl$_3$/δ)=4.35 (1H, H-1'), 3.86 (1H, H-3), 3.57 (1H, H-5'), 3.31 (1H, H-2'), 2.67 (1H, H-2), 2.5 (1H, H-3'). 2.30 (6H, 3'-N(CH$_3$)$_2$), 1.96 (1H, H-14a), 1.70 (1H, H-4'a), 1.56 (1H, H-14b), 1.30 (1H, H-4'b), 0.93 (3H, H-15).

$^{13}$C NMR (500 MHz; CDCl$_3$/δ)=175.8 (C-1), 105.3 (C-1'), 75.4 (C-3), 69.8 (C-5'), 68.9 (C-2') 64.6 (C-3') 44.7 (C-2), 39.6 (3'-N(CH$_3$)$_2$), 20.9 (C-14), 29.8 (C-4'), 10.4 (C-15).

MS (ES$^+$) m/z (%)=851.

EXAMPLE 10

5-O-Desosaminyl-9-deoxo-9-dihydro-9a-N-{N'-[4-(2-pyridylaminosulfonyl)phenyl]-carbamoyl}-9a-aza-9a-homoerithronolide A Analogously to the process disclosed in Example 3, from 1.15 g (2.0 mmol) 5-O-desosaminyl-9-deoxo-9-dihydro-9a-aza-9a-homoerithronolide A, 0.43 g (2.0 mmol) 4-(chlorosulfonyl)phenyl isocyanate and 0.4 g (4.2 mmol) 2-aminopyridine in 30 ml dry toluene 0.80 g pure 5-O-desosaminyl-9-deoxo-9-dihydro-9a-N-{N'-[4-(2-pyridylaminosulfonyl)phenyl]carbamoyl}-9a-aza-9a-homoerithronolide A was obtained with following spectral data.

$^1$H NMR (500 MHz; CDCl$_3$,δ)=8.30, 7.64 7.38, 7.64 (1H, aminopiridin), 4.34 (1H, H-1'), 3.84 (1H, H-3), 3.58 (1H, H-5'), 3.31 (1H, H-2'), 2.63 (1H, H-2), 2.6 (1H, H-3'), 2.29 (6H, 3'-N(CH$_3$)$_2$), 1.94 (1H, H-14a), 1.71 (1H, H-4'a), 1.55 (1H, H-14b), 1.29 (1H, H-4'b), 0.92 (3H, H-15).

$^{13}$C NMR (500 MHz; CDCl$_3$/δ)=141.5, 140.8, 114.5, 114.1 (aminopiridin), 105.4 (C-1'), 75.3 (C-3), 69.9 (C-5'), 68.9 (C-2') 64.6 (C-3') 44.7 (C-2), 39.6 (3'-N(CH$_3$)$_2$), 20.9 (C-14), 29.9 (C-4'), 10.4 (C-15).

MS (ES$^+$) m/z (%)=852.

EXAMPLE 11

5-O-Desosaminyl-9-deoxo-9-dihydro-9a-N-{N'-[4-(3,4-dimethyl-3-isoxazolylaminosulfonyl)phenyl]carbamoyl}-9a-aza-9a-homoerithronolide A Analogously to the process disclosed in Example 3, from 1.15 g (2.0 mmol) 5-O-desosaminyl-9-deoxo-9-dihydro-9a-aza-9a-homoerithronolide A, 0.43 g (2.0 mmol) 4-(chlorosulfonyl)phenyl isocyanate and 0.45 g (4.0 mmol) 5-amino-3,4-dimethylisoxazole in 30 ml dry toluene 0.75 g pure 5-O-desosaminyl-9-deoxo-9-dihydro-9a-N-{N'-[4-(3,4-dimethyl-3-isoxazolylaminosulfonyl)phenyl]carbamoyl}-9a-aza-9a-homoerithronolide A was obtained with following spectral data.

MS (ES$^+$) m/z (%)=870.

EXAMPLE 12

5-O-Desosaminyl-9-deoxo-9-dihydro-9a-N-{N'-[4-(5-methyl-3-isoxazolylaminosulfonyl)phenyl]carbamoyl)}-9a-aza-9a-homoerithronolide A Analogously to the process disclosed in Example 3, from 1.15 g (2.0 mmol) 5-O-desosaminyl-9-deoxo-9-dihydro-9a-aza-9a-homoerithronolide A, 0.43 g (2.0 mmol) 4-(chlorosulfonyl)phenyl isocyanate and 0.39 g (4.0 mmol) 3-amino-5-methylisoxazole in 30 ml dry toluene 0.7 g pure 5-O-desosaminyl-9-deoxo-9-dihydro-9a-N-{N'-[4-(5-methyl-3-isoxazolylaminosulfonyl)phenyl]carbamoyl}-9a-aza-9a-homoerithronolide A was obtained with following spectral data.

$^1$H NMR (500 MHz; CDCl$_3$/δ)=4.36 (1H, H-1'), 3.87 (1H, H-3), 3.56 (1H, H-5'), 3.32 (1H, H-2'), 2.65 (1H, H-2), 2.48 (1H, H-3'), 2.32 (6H, 3'-N(CH$_3$)$_2$), 1.95 (1H, H-14a), 1.70 (1H, H-4'a), 1.55 (1H, H-14b), 1.30 (1H, H-4'b), 0.90 (3H, H-15).

$^{13}$C NMR (500 MHz; CDCl$_3$/δ)=105.6 (C-1'), 74.6 (C-3), 69 (C-5'), 69.3 (C-2') 64.6 (C-3') 44 (C-2), 40.1 (3'-N (CH$_3$)$_2$), 21.4 (C-14), 30.2 (C-4'), 10.8 (C-15).

MS (ES$^+$) m/z (%)=856.

What is claimed is:

1. A compound of formula 1,

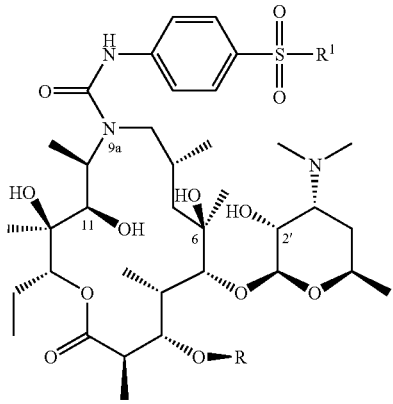

(1)

wherein R represents H or cladinosyl moiety, and R$^1$ represents chloro, amino, phenylamino, 2-pyridylamino, 3,4-dimethyl-5-isoxazolylamino or 5-methyl-3-isoxazolylamino group, or a pharmaceutically acceptable salt thereof.

2. A compound according to claim 1, characterized in that R$^1$ represents chloro group and R represents cladinosyl moiety.

3. A compound according to claim 1 characterized in that R$^1$ represents chloro group, and R represents H.

4. A compound according to claim 1 where R$^1$ represents amino group, and R represents cladinosyl moiety.

5. A compound according to claim 1, characterized in that R$^1$ represents phenylamino group, and P represents cladinosyl group.

6. A compound according to claim 1, characterized in that R$^1$ represents 2-pyridylamino group, and R represents cladinosyl group.

7. A compound according to claim 1, characterized in that R$^1$ represents 3,4-dimethyl-5-isoxazolylamino group, and R represents cladinosyl moiety.

8. A compound according to claim 1, characterized in that R$^1$ represents 5-methyl-3-isoxazolylamino group, and R represents cladinosyl group.

9. A compound according to claim 1, characterized in that R$^1$ represents amino group and R represents H.

10. A compound according to claim 1, characterized in that R$^1$ represents phenylamino group, and R represents H.

11. A compound according to claim 1, characterized in that R$^1$ represents 2-pyridylamino group, and R represents H.

12. A compound according to claim 1, characterized in that R$^1$ represents 3,4-dimethyl-5-isoxazolylamino group, and R represents H.

13. A compound according to claim 1, characterized in that R$^1$ represents 5-methyl-3-isoxazolylamino group and R represents H.

14. A process for the preparation of a compound of formula 1,

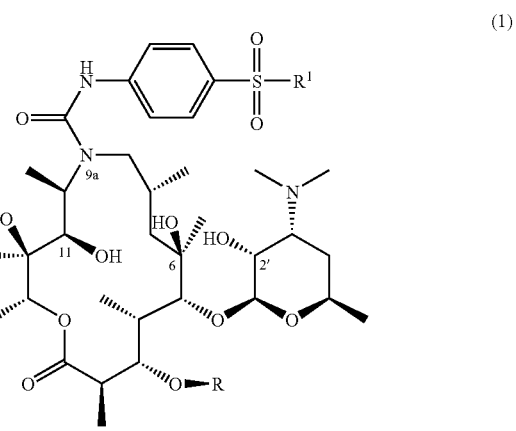

(1)

wherein R$^1$ represents amino, phenylamino, 2-pyridylamino, 3,4-dimethyl-5-isoxazolylamino or 5-methyl-3-isoxazolylamino group and R represents H or cladinosyl group, comprising reacting a compound of formula 2

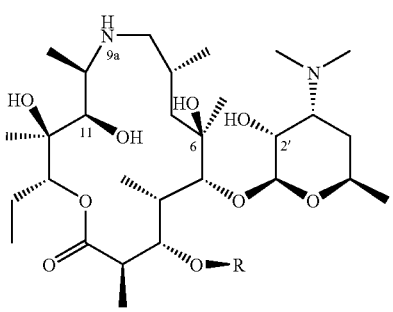

(2)

wherein R represents H or cladinosyl group, with 4-(chlorosulfonyl)phenyl isocyanate formula 3,

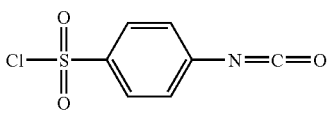

3 to form a compound of formula 1 wherein R is H or cladinosyl group and R$^1$ is chloro; reacting a compound of formula 1 wherein R is H or cladinosyl group and $R^1$ is chloro with ammonia or amine of general formula 4, $R^2$—$NH_2$     4 wherein $R^2$ represents H, phenyl, 2-pyridyl, 3,4-dimethyl-5-isoxazolyl or 5-methyl-3-isoxazolyl group, in toluene, xylene or some other aprotic solvent, at a temperature 0-110° C. to form a compound of formula 1 wherein R is H or cladinosyl and $R^1$ is amino, phenylamino, 2-pyridylamino, 3,4-dimethyl-5-isoxazolylamino or 5-methyl-3-isoxazolylamino.

15. Pharmaceutical composition comprising a pharmaceutically acceptable carrier and an antibacterially effective amount of a compound according to claim 1.

16. A method for inhibiting bacterial growth in vitro on a surface or in a substance comprising applying to said surface or substance a bactericially effective amount of a compound according to claim 1.

17. The method of claim 16 wherein the surface is selected from the group consisting of a wall, a room, and a medical instrument.

18. The method of claim 16 wherein the substance is selected from the group of wall coatings and wooden coatings.

19. A process for the preparation of a compound of formula 1,

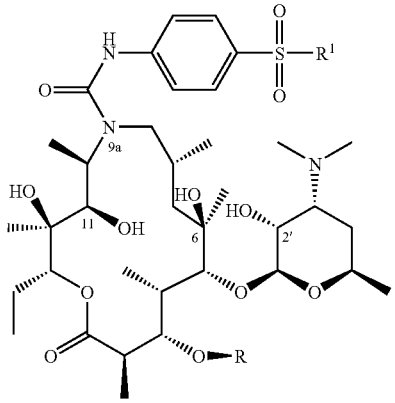

wherein $R^1$ represents chloro and R represents H or cladinosyl group, comprising reacting a compound of formula 2

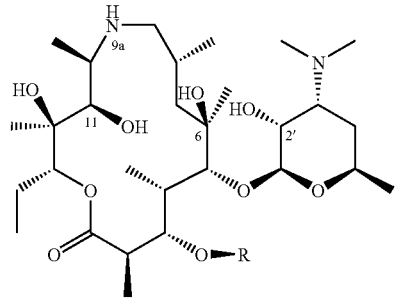

wherein R represents H or cladinosyl group with 4-(chlorosulfonyl)phenyl isocyanate formula 3,

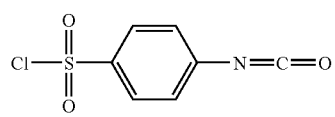

to form a compound of formula 1 wherein R is H or cladinosyl and $R^1$ is chloro.

20. A compound of general formula 1,

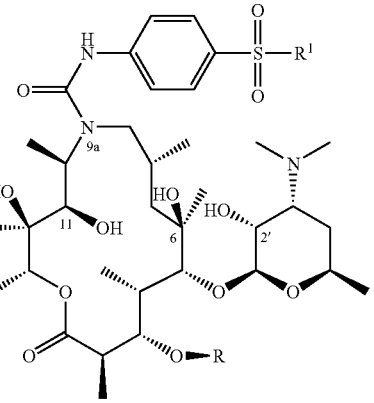

wherein R represents H or cladinosyl moiety, and $R^1$ represents chloro, amino, phenylamino, 2-pyridylamino, 3,4-dimethyl-5-isoxazolylamino or 5-methyl-3-isoxazolylamino group.

* * * * *

UNITED STATES PATENT AND TRADEMARK OFFICE
CERTIFICATE OF CORRECTION

PATENT NO. : 7,365,056 B2
APPLICATION NO. : 10/534628
DATED : April 29, 2008
INVENTOR(S) : Nedjeljko Kujundzic, Mirjana Bukvic Krajacic and Karmen Brajsa It is certified that error appears in the above-identified patent and that said Letters Patent is hereby corrected as shown below:

In Column 9, line 57, "P" should read "R"
In Column 9, line 60, "ciadinosyl" should read "cladinosyl"
In Column 11, line 10, After 110° C, delete "."

Signed and Sealed this

Twenty-fourth Day of February, 2009

JOHN DOLL
*Acting Director of the United States Patent and Trademark Office*